US00PP34310P2

(12) United States Plant Patent
Smith

(10) Patent No.: US PP34,310 P2
(45) Date of Patent: Jun. 7, 2022

(54) ***CHRYSANTHEMUM* PLANT NAMED 'CIFZ0085'**

(50) Latin Name: ***Chrysanthemum* x *morifolium***
Varietal Denomination: CIFZ0085

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/233,872

(22) Filed: Apr. 19, 2021

(51) Int. Cl.
*A01H 5/02* (2018.01)
*A01H 6/14* (2018.01)

(52) U.S. Cl.
USPC ..... Plt./287

(58) Field of Classification Search
USPC ..... Plt./287, 289, 290
CPC ... A01H 5/02; A01H 5/00; A01H 6/14; A01H 6/1424
See application file for complete search history.

(56) References Cited

U.S. PATENT DOCUMENTS

PP25,012 P3 * 10/2014 Blom ..... A01H 6/1424 Plt./287
PP31,323 P2 * 1/2020 Smith ..... A01H 5/02 Plt./290

* cited by examiner

*Primary Examiner* — June Hwu
(74) *Attorney, Agent, or Firm* — Dale Skalla

(57) ABSTRACT

A new garden type *Chrysanthemum* plant named 'CIFZ0085' particularly distinguished by its medium to large size plant with mound plant habit, a medium to large size decorative flower, golden yellow flower color with bronze petal tips and a natural season response in the end of September.

1 Drawing Sheet

Figure 1:
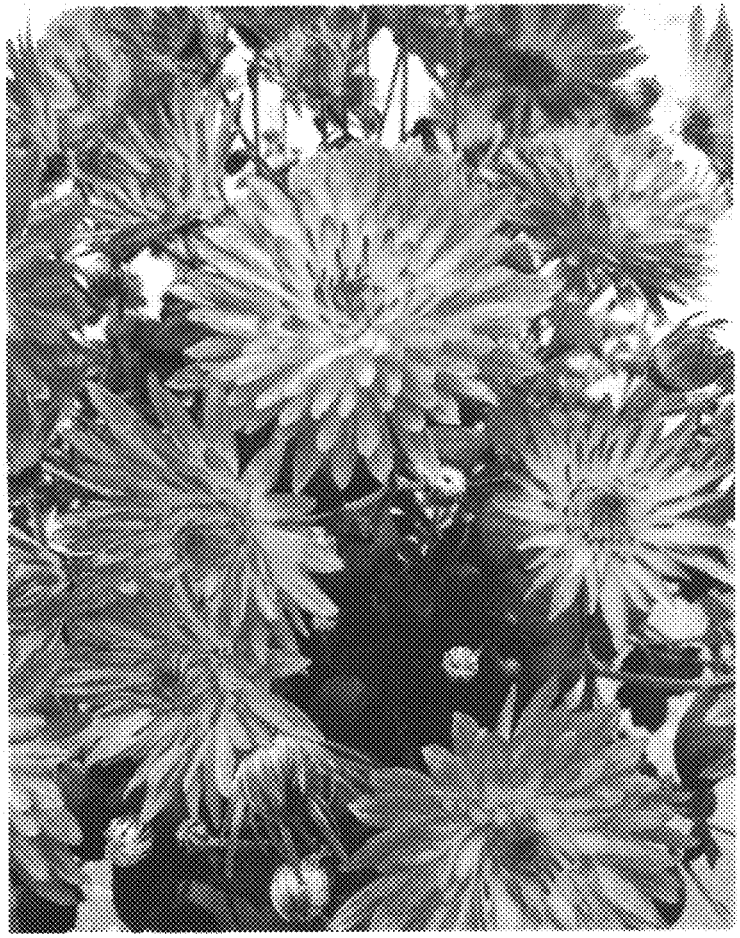

Latin name of the genus and species of the plant claimed: *Chrysanthemum* x *morifolium*.

Varietal denomination: 'CIFZ0085'.

BACKGROUND OF THE NEW PLANT

The present invention comprises a new *Chrysanthemum*, botanically known as *Chrysanthemum* x *morifolium*, and hereinafter referred to by the variety name 'CIFZ0085'.

'CIFZ0085' is a product of a planned breeding program. The new cultivar has medium to large size plant with mound plant habit, a medium to large size decorative flower, golden yellow flower color with bronze petal tips and a natural season response in the end of September.

'CIFZ0085' originated from a cross made in October 2014 in Enkhuizen, The Netherlands. Seeds were sown in November 2016 in Gilroy, Calif. and 'CIFZ0085' was selected from the resulting population on March 28, 2017 in Alva, Fla.

The female parent was the variety 'Zanmufrenzy', U.S. Plant Pat. No. 25,012.

TABLE 1

Characteristics of the female parent, compared to 'CIFZ0085':

| Trait | 'CIFZ0085' | 'Zanmufrenzy' |
|---|---|---|
| Natural response: | One week later | One week earlier |
| Blackcloth response: | Similar | Similar |
| Flower size: | Similar | Similar |
| Flower color: | Golden yellow with bronze ray petal tips | Bright coral pink without bicolor effect |

TABLE 1-continued

Characteristics of the female parent, compared to 'CIFZ0085':

| Trait | 'CIFZ0085' | 'Zanmufrenzy' |
|---|---|---|
| Flower type: | Similar | Similar |
| Plant size: | 19-21 cm in height | Average height is 35 cm |
| Plant habit: | Rounder | More irregular |
| Flower longevity: | 20% longer | 20% shorter |
| Flowering uniformity: | More uniform flowering | Less uniform flowering |

The male parent was an unpatented proprietary seedling '09-M178', pink/lavender and white daisy bicolor.

TABLE 2

Characteristics of the male parent, compared to 'CIFZ0085':

| Trait | CIFZ0085 | '09-M178' |
|---|---|---|
| Natural response: | 2 weeks slower | 2 weeks faster |
| Blackcloth response: | ½ week faster | ½ week slower |
| Flower size: | Similar | Similar |
| Flower color: | Golden yellow with bronze petal tips | Dark Pink/lavender and white bicolor |
| Flower type: | Decorative | Daisy |
| Plant size: | Larger | Smaller |
| Plant habit: | Similar | Similar |
| Flowering uniformity: | Similar | Similar |

The first act of asexual reproduction of 'CIFZ0085' was accomplished when vegetative stem cuttings were propagated from the initial selection in May 2017 in Alva, Fla.

BRIEF SUMMARY OF INVENTION

Horticultural examination of plants grown from cuttings of the plant initiated in May 2017 and continuing thereafter, has demonstrated that the combination of characteristics as herein disclosed for 'CIFZ0085' are firmly fixed and are retained through successive generations of asexual reproduction.

'CIFZ0085' has not been observed under all possible environmental conditions. The phenotype may vary significantly with variations in environment such as temperature, light intensity and day length.

A Plant Breeder's Right for this cultivar has not yet been applied for. 'CIFZ0085' has not been made publicly available prior to the effective filing date of this application, notwithstanding any disclosure that may have been made less than one year prior to the effective filing date of this application by the inventor or another who obtained 'CIFZ0085' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0085' with colors being as true as possible with an illustration of this type.

Figure 2:
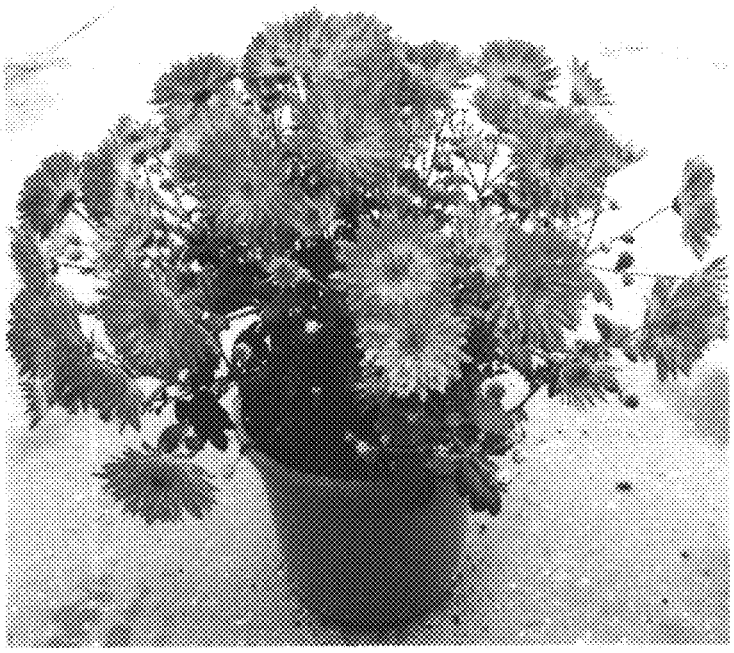

The photographic drawing shows in FIG. 1 a close view of flower of the new variety and in FIG. 2 a flowering plant from an indoor trial.

The aforementioned photographs: FIG. 1, as well as FIG. 2 were taken in March 2021 both showing a plant from the same blackcloth indoor trial in Enkhuizen, The Netherlands.

These plants were about 10 weeks of age. One rooted cutting per pot had been planted in a one gallon pot, not pinched in week 53, 2020 and black clothed from week 3. Plants started flowering mid March 2021.

DETAILED BOTANICAL DESCRIPTION

The measurements were taken in Gilroy, Calif. in September 2020 on plants from an indoor blackcloth trial in Gilroy, Calif.

Color references are made to The Royal Horticultural Society Colour Chart (RHS) 2015.

TABLE 3

| Trait | 'CIFZ0085' | 'CIFZ0070', U.S. Plant Pat. No. 31,323 |
|---|---|---|
| Natural response - North: | ½ week faster | ½ week slower |
| Natural response - South: | 1 week faster | 1 week slower |
| Blackcloth response: | Similar | Similar |
| Mature inflorescence diameter: | 4.6 cm | 4.4 cm |
| Flower color: | Golden yellow with bronze tips | Orange yellow with darker centre |
| Flower type: | Similar | Similar |
| Plant size: | Similar | Similar |
| Plant habit: | Similar | Similar |
| Flower longevity: | Slightly less | Slightly more |
| Plant strength: | Stronger | Weaker |

TABLE 4

| Trait | 'CIFZ0085' | 'Conaco Gold', Unpatented |
|---|---|---|
| Natural response: | Similar | Similar |
| Blackcloth response: | One week faster | One week slower |
| Flower size: | ¼ inch smaller | ¼ inch larger |
| Flower color: | Similar | Similar |
| Flower type: | Similar | Similar |
| Plant size: | Larger | Smaller |
| Plant habit: | Similar | Similar |
| Flower longevity: | 20% longer | 20% shorter |
| Flowering uniformity: | Less uniform flowering | More uniform flowering |

Plant:

*Form, growth and habit.*—Herbaceous garden-type, stems Upright and outwardly spreading, freely branching, strong and moderately vigorous growth habit.

*Plant height* (*above soil*).—17-18 cm.

*Plant height* (*inflorescence included*).—19-21 cm.

*Plant width.*—28 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 137A.

*Immature leaf, color lower surface.*—RHS 137C.

*Mature leaf, color, upper surface.*—RHS NN137A.

*Mature leaf, color lower surface.*—RHS NN137C.

*Length.*—3.5 cm.

*Width.*—2.8 cm.

*Shape.*—Ovate, with distinct lobes.

*Base shape.*—Attenuate.

*Apex shape.*—Mucronate.

*Margin.*—5-lobed (palmate), edge dentate.

*Number of margin indentations.*—Medium.

*Depth of margin indentations.*—Shallow.

*Leaf length terminal lobe relative to total leaf length.*—Short.

*Leaf depth lower lateral sinus.*—Shallow.

*Texture, upper surface.*—Bifid hairs.

*Texture, lower surface.*—Bifid hairs.

*Color of veins, upper surface.*—RHS 138B.

*Color of veins, lower surface.*—RHS 138A.

*Pattern of veining.*—Palmate.

*Petiole color.*—RHS 137A.

*Petiole length.*—1.0-1.1 cm.

*Diameter.*—0.2-0.3 cm.

*Texture.*—Bifid hairs.

*Presence of stipules.*—Yes.

*If present, size of stipules.*—Small.

Stem:

*Quantity of main branches per plant.*—6.

*Color of stem.*—RHS 138A.

*Length of stem.*—10-12 cm.

*Diameter.*—0.6 cm.

*Length of internodes.*—2.0-2.5 cm.

*Texture.*—Bifid hairs.

*Color of peduncle.*—RHS 138A.

*Length of peduncle.*—3.0-3.5 cm.

*Peduncle diameter.*—0.3 cm.
*Texture.*—Bifid hairs.

Inflorescence:
*Type.*—Compositae, solitary, decorative-type inflorescences borne terminally above foliage, ligulate ray florets arranged acropetally on a capitulum giving a double flower.
*Quantity of short days to flowering* (*response time*).—Approximately 7 weeks.
*Quantity of inflorescences per plant.*—108-110 with many small buds developing.
*Lastingness of individual blooms on the plant.*—About six weeks from first color.
*Fragrance.*—Slightly spicy.

Bud (when showing color):
*Color.*—RHS 10B with RHS N34A at top.
*Length.*—1.1-1.3 cm.
*Width.*—0.7-0.8 cm.
*Shape.*—Oblate.

Immature inflorescence (at moment of opening):
*Diameter.*—2.0 cm.
*Color of ray florets, upper surface.*—RHS 12A; with RHS N34A at tips.
*Color of ray florets, lower surface.*—RHS 12B; with RHS N34A at tips.

Mature inflorescence:
*Diameter.*—4.6 cm.
*Depth.*—1.1 cm.
*Total diameter of disc.*—No disc present.
*Receptacle color.*—RHS NN137A.
*Receptacle height.*—0.6 cm.
*Receptacle diameter.*—1.2 cm.
*Length of corolla tube.*—Medium.

Ray florets:
*Average quantity of florets.*—60-120 in several whorls.
*Color of florets, upper surface.*—RHS N34A; RHD 12A at base.
*Color lower surface.*—RHS 12B; some spots of RHS N34A at tips.
*Length.*—1.6 cm.
*Width/diameter.*—0.4 cm.
*Shape.*—Elliptical.
*Apex shape.*—Mostly obtuse and dentate.
*Base shape.*—Tube.
*Margin.*—Entire. Small incisions may be present at tip.
*Margin.*—type of rolling Weakly involute.
*Texture, upper surface.*—Papillate.
*Lower surface.*—Papillate.
*Ray floret corolla tube shape.*—Flattened.
*Ribs present.*—Yes.
*Number of keels.*—2.
*Profile at widest point.*—Moderately convex.
*Longitudinal axis shape.*—Reflexing.
*Longitudinal axis curvature strength of the inner and outer rows.*—Weak.

Disc florets:
*Number of disc florets.*—No disc present.

Inflorescence (at moment of senescence):
*Color of ray florets, upper surface.*—RHS N34A; RHS 7A at base.
*Color of ray florets, lower surface.*—RHS 8A.

Phyllaries:
*Quantity.*—20.
*Color, upper surface.*—RHS 143C.
*Color, lower surface.*—RHS 143A.
*Length.*—0.6 cm.
*Width.*—0.1-0.2 cm.
*Shape.*—Lanceolate.
*Apex shape.*—Acute.
*Base.*—Fused.
*Margins.*—Entire.
*Texture, upper surface.*—Glabrous.
*Texture, lower surface.*—Canescent.

Reproductive organs:
*Pistil.*—One.
*Length.*—0.4 cm.
*Style color.*—RHS 150C.
*Style length.*—0.3 cm.
*Stigma color.*—RHS 7D.
*Stigma shape.*—Bi-parted.
*Ovary color.*—RHS 145C.
*Ovary length.*—0.2 cm.
*Ovary width.*—0.1 cm.

Androecium: As no disc florets are present, no androecium developed.
*Disease/pest resistance.*—Has not been determined to date.
*Hardiness.*—Has not been determined to date.

What is claimed is:

1. A new and distinct variety of *Chrysanthemum* plant named 'CIFZ0085' substantially as illustrated and described herein.

* * * * *